(12) United States Patent
Williams et al.

(10) Patent No.: US 7,962,289 B2
(45) Date of Patent: Jun. 14, 2011

(54) SYSTEM, METHOD, AND COMPUTER PRODUCT FOR EXON ARRAY ANALYSIS

(75) Inventors: Alan J. Williams, Albany, CA (US); Charles W. Sugnet, El Cerrito, CA (US); James H. Gorrell, Emeryville, CA (US)

(73) Assignee: Affymetrix, Inc., Santa Clara, CA (US)

( * ) Notice: Subject to any disclaimer, the term of this patent is extended or adjusted under 35 U.S.C. 154(b) by 1094 days.

(21) Appl. No.: 11/421,941

(22) Filed: Jun. 2, 2006

(65) Prior Publication Data

US 2006/0275805 A1      Dec. 7, 2006

Related U.S. Application Data

(60) Provisional application No. 60/686,627, filed on Jun. 2, 2005, provisional application No. 60/756,097, filed on Jan. 4, 2006.

(51) Int. Cl.
*G06F 19/00* (2006.01)
*G06F 15/00* (2006.01)
*C12N 15/11* (2006.01)

(52) U.S. Cl. ............................. 702/19; 700/1; 536/24.3

(58) Field of Classification Search ........................ None
See application file for complete search history.

(56) References Cited

U.S. PATENT DOCUMENTS

2002/0147512 A1 *   10/2002   Bernhart et al. ................. 700/90

OTHER PUBLICATIONS

Tusher et al. Significance analysis of microarrays applied to the ionizing radiation response Proc. Natl. Acad. Sci. USA vol. 98, pp. 5116-5121 (2001).*
Johnson et al. Genome-Wide Survey of Human Alternative Pre-mRNA Splicing with Exon Junction Microarrays Science vol. 302 pp. 2141-2144 (2003).*
Schageman et al. MarC-V: A Spreadsheet-Based Tool for Analysis, Normalization, and Visualization of Single cDNA Microarray Experiments BioTechniques vol. 32 pp. 338-340, 343, and 344 (2002).*
Tseng et al. Issues in cDNA microarray analysis: quality filtering, channel normalization, models of variations and assessment of gene effects Nucleic Acids Research vol. 29, pp. 2549-2557 (2001).*
Thallinger et al. Information management systems for pharmacogenomics Pharmacogenomics vol. 3, pp. 651-667 (2002).*
Parrish et al. Effect of Normalization on Significance Testing for Oligonucleotide Microarrays. Journal of Biopharmaceutical Statistics vol. 14, pp. 575-589 (2004).*

* cited by examiner

*Primary Examiner* — John S Brusca
(74) *Attorney, Agent, or Firm* — Steven M. Yee; Thomas J. Siepmann

(57) ABSTRACT

In one embodiment, a method for analyzing data generated by probe arrays is described that comprises receiving user selections of two or more data files and an identification of one or more subsets of intensity values acquired from a biological probe array. The method includes iteratively opening each data file, identifying the selected subset of intensity values associated with each open data file, determining parameters for processing, storing the parameters and the identified intensity values, and closing the open data file prior to the subsequent iteration. The method then includes processing the stored intensity values using the parameters to identify one or more biological events.

25 Claims, 5 Drawing Sheets

SYSTEM, METHOD, AND COMPUTER PRODUCT FOR EXON ARRAY ANALYSIS

RELATED APPLICATIONS

The present application claims priority from U.S. Provisional Patent Application Ser. No. 60/686,627, titled "System, Method and Computer Product for Exon Array Analysis", filed Jun. 2, 2005; and U.S. Provisional Patent Application Ser. No. 60/756,097, titled "System, Method and Computer Product for Exon Array Analysis", filed Jan. 4, 2006, each of which is hereby incorporated by reference herein in it's entirety for all purposes.

BACKGROUND

1. Field of the Invention

The present invention relates to systems and methods for examining biological material. In particular, the invention relates to providing a simplified and highly flexible architecture for the analysis of data from scanned biological probe arrays, in particular arrays designed for a specialized purpose. To effectively address the specialized needs of emerging technology it is important to tailor the analysis tools so that the most effective and efficient methods are applied to data generated from the particular technology in an intuitive and easily manageable format.

2. Related Art

Synthesized nucleic acid probe arrays, such as Affymetrix GeneChip® probe arrays, and spotted probe arrays, have been used to generate unprecedented amounts of information about biological systems. For example, the GeneChip® Human Genome U133 Pus 2.0 Array available from Affymetrix, Inc. of Santa Clara, Calif., is comprised of one microarray containing 1,300,000 oligonucleotide features covering more than 47,000 transcripts and variants that include 38,500 well characterized human genes. Other examples of GeneChip® arrays are targeted to provide data aimed at more specialized areas such as what may be referred to as Single Nucleotide Polymorphisms (SNPs) provided by the Affymetrix 10K, 100K, or 500K GeneChip® Probe Arrays, or all exon arrays that specialize in the analysis of alternative splicing events. Analysis of data from such microarrays may lead to the development of new drugs and new diagnostic tools.

SUMMARY OF THE INVENTION

Systems, methods, and products to address these and other needs are described herein with respect to illustrative, non-limiting, implementations. Various alternatives, modifications and equivalents are possible. For example, certain systems, methods, and computer software products are described herein using exemplary implementations for analyzing data from arrays of biological materials, in particular in relation to data from Affymetrix® GeneChip® probe arrays. However, these systems, methods, and products may be applied with respect to many other types of probe arrays and, more generally, with respect to numerous parallel biological assays produced in accordance with other conventional technologies and/or produced in accordance with techniques that may be developed in the future. For example, the systems, methods, and products described herein may be applied to parallel assays of nucleic acids, PCR products generated from cDNA clones, proteins, antibodies, or many other biological materials. These materials may be disposed on slides (as typically used for spotted arrays), on substrates employed for Gene-Chip® arrays, or on beads, optical fibers, or other substrates or media, which may include polymeric coatings or other layers on top of slides or other substrates. Moreover, the probes need not be immobilized in or on a substrate, and, if immobilized, need not be disposed in regular patterns or arrays. For convenience, the term "probe array" will generally be used broadly hereafter to refer to all of these types of arrays and parallel biological assays.

In one embodiment, a method for analyzing data generated by probe arrays is described that comprises receiving user selections of two or more data files and an identification of one or more subsets of intensity values acquired from a biological probe array. The method includes iteratively opening each data file, identifying the selected subset of intensity values associated with each open data file, determining parameters for processing, storing the parameters and the identified intensity values, and closing the open data file prior to the subsequent iteration. The method then includes processing the stored intensity values using the parameters to identify one or more biological events.

In addition, a system for analyzing data generated by probe arrays is described that comprises a scanner that acquires pixel intensity values from multiple probe arrays; and a computer that includes a first application stored for execution in system memory that generates a data file associated with each of the probe arrays comprising a probe intensity value for each of a plurality of probes using the pixel intensity values; and a second application stored for execution in system memory that performs a method that includes receiving user selections of two or more data files and an identification of one or more subsets of intensity values acquired from a biological probe array. The method includes iteratively opening each data file, identifying the selected subset of intensity values associated with each open data file, determining parameters for processing, storing the parameters and the identified intensity values, and closing the open data file prior to the subsequent iteration. The method then includes processing the stored intensity values using the parameters to identify one or more biological events.

Also, a method for analyzing data generated by probe arrays is described that comprises receiving user selections of two or more data files and an identification of intensity values within each data file that were acquired from a biological probe array. The method includes iteratively opening each data file, identifying and storing the intensity values selected by the user for that data file in one or more data objects, and closing the open data file prior to the subsequent iteration. The method then includes processing each of the stored intensity values from the data objects to identify one or more biological events.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 160 appears first in FIG. 1). In functional block diagrams, rectangles generally indicate functional elements and parallelograms generally indicate data. In method flow charts, rectangles generally indicate method steps and diamond shapes generally indicate decision elements. All of these conventions, however, are intended to be typical or illustrative, rather than limiting.

DETAILED DESCRIPTION a) General

Figure 1:
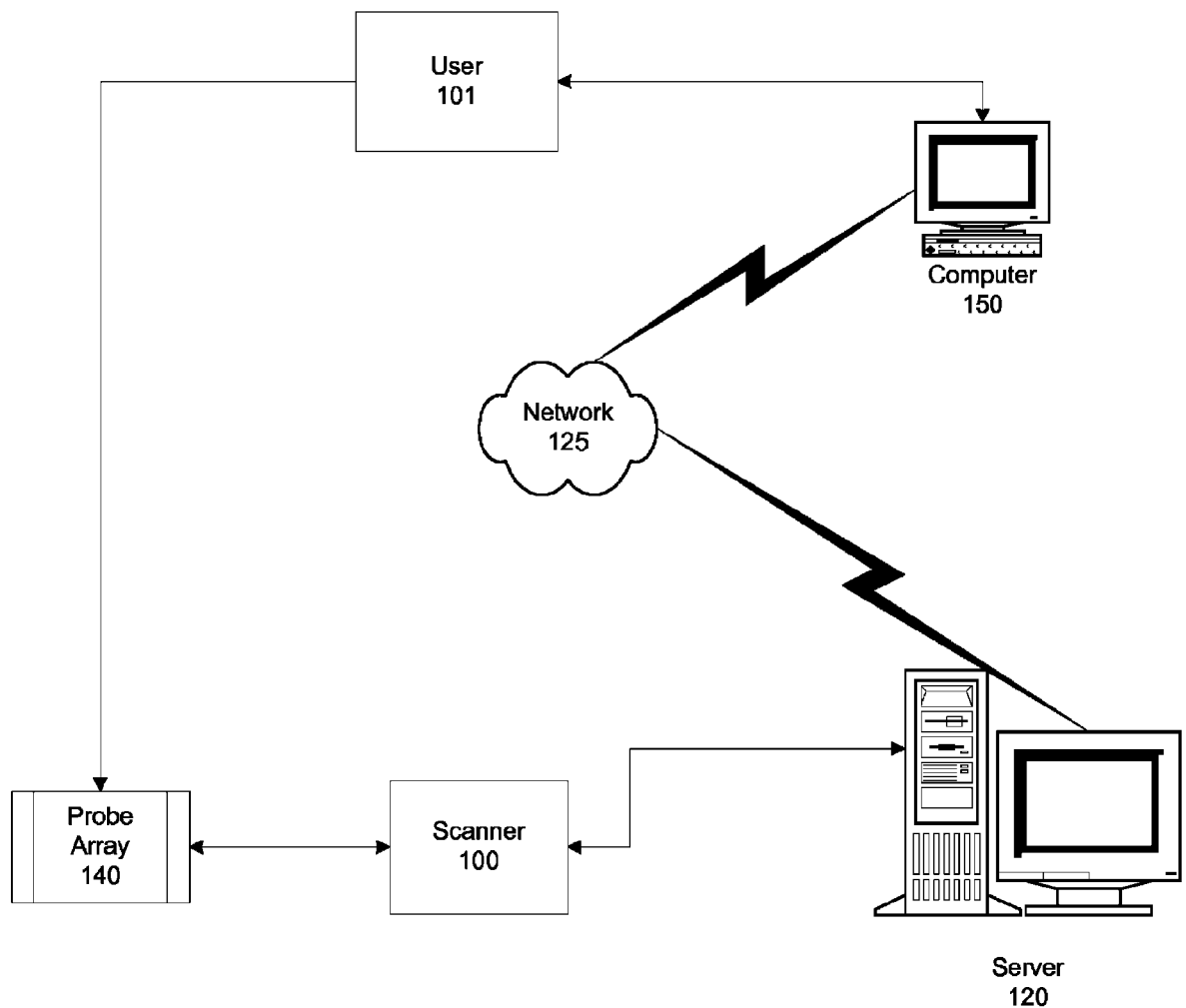
FIG. 1 is a functional block diagram of one embodiment of a computer and a server enabled to communicate over a network, as well as a probe array and scanner instrument.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, N.Y., Gait, "*Oligonucleotide Synthesis: A Practical Approach*" 1984, IRL Press, London, Nelson and Cox (2000), Lehninger, *Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252, 743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,945,334, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285 (International Publication Number WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871, 928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159, 4,965, 188, and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference. Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491 (U.S. Patent Application Publication 20030096235), Ser. No. 09/910,292 (U.S. Patent Application Publication 20030082543), and Ser. No. 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854,5, 578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194, 10/913,102, 10/846,261, 11/260,617 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621, 10/063,559 (United States Publication No. 20020183936), Ser. Nos. 10/065,856, 10/065,868, 10/328,818, 10/328,872, 10/423,403, and 60/482,389.

b) Definitions

The term "array" as used herein refers to an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

The term "biomonomer" as used herein refers to a single unit of biopolymer, which can be linked with the same or other biomonomers to form a biopolymer (for example, a single amino acid or nucleotide with two linking groups one or both of which may have removable protecting groups) or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

The term "biopolymer" or "biological polymer" as used herein is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

The term "biopolymer synthesis" as used herein is intended to encompass the synthetic production, both organic and inorganic, of a biopolymer. Related to a biopolymer is a "biomonomer".

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complex population or mixed population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "effective amount" as used herein refers to an amount sufficient to induce a desired result.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization conditions" as used herein will typically include salt concentrations of less than about 1M, more usually less than about 500 mM and preferably less than about 200 mM. Hybridization temperatures can be as low as 5.degree. C., but are typically greater than 22.degree. C., more typically greater than about 30.degree. C., and preferably in excess of about 37.degree. C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

Hybridizations, e.g., allele-specific probe hybridizations, are generally performed under stringent conditions. For example, conditions where the salt concentration is no more than about 1 Molar (M) and a temperature of at least 25 degrees-Celsius (° C.), e.g., 750 mM NaCl, 50 mM NaPhosphate, 5 mM EDTA, pH 7.4 (5×SSPE) and a temperature of from about 25 to about 30° C.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (e.g., total cellular) DNA or RNA.

The term "initiation biomonomer" or "initiator biomonomer" as used herein is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, and antibodies.

The term "linkage disequilibrium or allelic association" as used herein refers to the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

The term "mixed population" as used herein refers to a complex population.

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA" or "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library or array" as used herein refers to an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate.

The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "primer" as used herein refers to a single-stranded oligonucleotide capable of acting as a point of initiation for template-directed DNA synthesis under suitable conditions e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

c) Embodiments of the Present Invention

Embodiments of an analysis system comprising an analysis application are described herein that provide specialized methods and tools for the analysis of specialized probe arrays. In particular, embodiments are described that provide systems and methods for the analysis of mRNA expression at the level of individual exons.

Probe Array 140: An illustrative example of probe array 140 is provided in FIGS. 1, 2, and 3. Descriptions of probe arrays are provided above with respect to "Nucleic Acid Probe arrays" and other related disclosure. In various implementations, probe array 140 may be disposed in a cartridge or housing such as, for example, the GeneChip® probe array available from Affymetrix, Inc. of Santa Clara Calif. Examples of probe arrays and associated cartridges or housings may be found in U.S. Pat. Nos. 5,945,334, 6,287,850, 6,399,365, 6,551,817, each of which is also hereby incorporated by reference herein in its entirety for all purposes. In addition, some embodiments of probe array 140 may be associated with pegs or posts, where for instance probe array 140 may be affixed via gluing, welding, or other means known in the related art to the peg or post that may be operatively coupled to a tray, strip or other type of similar substrate. Examples with embodiments of probe array 140 associated with pegs or posts may be found in U.S. patent Ser. No. 10/826,577, titled "Immersion Array Plates for Interchangeable Microtiter Well Plates", filed Apr. 16, 2004, which is hereby incorporated by reference herein in its entirety for all purposes.

Embodiments of the presently described invention may be particularly suited to process and analyze data generated from specialized embodiments of probe array 140. One such embodiment includes a probe array comprising a plurality of probe sets, where each probe set interrogates target molecules associated with an exon region. For example, each exon region is associated with a gene or functional region and may comprise one or more "probe selection regions" where the boundaries of the exon region may be defined by sequence characteristics that includes what may be referred to as internal splice sites, Poly Adenylation sites, and Coding Sequence (CDS) start and stop positions. In some cases the probe selection regions may be identified by other sequence characteristics such as what may be referred to as transcript start and stop positions, and splice site boundaries associated with known cDNA species showing a high degree of what is referred to as synteny with the exon region. In the present example, the gene or functional regions may be known through experimental evidence or predicted. Those of ordinary skill in the related art will appreciate that there are many methods and applications available that perform gene prediction functions, some of which may specialize on predictions made using certain criteria such as structural or functional criteria.

Continuing with the present example, a probe set may comprise one or more probes that interrogate a probe selection region. Some embodiments of such a probe array may include over 5 million probes that interrogate molecules associated with over 1.4 million probe selection regions.

Scanner 100: Labeled targets hybridized to probe arrays may be detected using various devices, sometimes referred to as scanners, as described above with respect to methods and apparatus for signal detection. An illustrative device is shown in FIG. 1 as scanner 100. For example, scanners image the targets by detecting fluorescent or other emissions from labels associated with target molecules, or by detecting transmitted, reflected, or scattered radiation. A typical scheme employs optical and other elements to provide excitation light and to selectively collect the emissions.

For example, scanner 100 provides a signal representing the intensities (and possibly other characteristics, such as color that may be associated with a detected wavelength) of the detected emissions or reflected wavelengths of light, as well as the locations on the substrate where the emissions or reflected wavelengths were detected. Typically, the signal includes intensity information corresponding to elemental sub-areas of the scanned substrate. The term "elemental" in this context means that the intensities, and/or other characteristics, of the emissions or reflected wavelengths from this area each are represented by a single value. When displayed as an image for viewing or processing, elemental picture elements, or pixels, often represent this information. Thus, in the present example, a pixel may have a single value representing the intensity of the elemental sub-area of the substrate from which the emissions or reflected wavelengths were scanned. The pixel may also have another value representing another characteristic, such as color, positive or negative image, or other type of image representation. The size of a pixel may vary in different embodiments and could include a 2.5 μm, 1.5 μm, 1.0 μm, or sub-micron pixel size. Two examples where the signal may be incorporated into data are data files in the form *.dat or *.tif as generated respectively by instrument control and image analysis applications 372 (described in greater detail below) that may include the Affymetrix® Microarray Suite software (described in U.S. patent application Ser. No. 10/219,882, which is hereby incorporated by reference herein in its entirety for all purposes) or Affymetrix® GeneChip® Operating Software (described in U.S. patent application Ser. No. 10/764,663, which is hereby incorporated by reference herein in its entirety for all purposes) based on images scanned from GeneChip® arrays.

Embodiments of scanner 100 may employ various elements and optical architectures for detection. For instance, some embodiments of scanner 100 may employ what is referred to as a "confocal" type architecture that may include the use of photomultiplier tubes to as detection elements. Alternatively, some embodiments of scanner 100 may employ a CCD type (referred to as a Charge Coupled Device) architecture using what is referred to as a CCD or cooled CCD cameras as detection elements. Further examples of scanner systems that may be implemented with embodiments of the present invention include U.S. patent application Ser. No. 10/389,194, 10/846,261, 10/913,102, and 11/260,617; each of which are incorporated by reference above; and U.S. patent application Ser. No. 11/379,641, titled "Methods and Devices for Reading Microarrays", filed Apr. 21, 2006, which is hereby incorporated by reference herein in it's entirety for all purposes.

Computer 150: An illustrative example of computer 150 is provided in FIG. 1 and also in greater detail in FIG. 2. Computer 150 may be any type of computer platform such as a workstation, a personal computer, a server, or any other present or future computer. Computer 150 typically includes known components such as a processor 255, an operating system 260, system memory 270, memory storage devices 281, and input-output controllers 275, input-output devices 240, and display devices 245. Display devices 245 may include display devices that provides visual information, this information typically may be logically and/or physically organized as an array of pixels. An interface controller may also be included that may comprise any of a variety of known or future software programs for providing input and output interfaces such as for instance interfaces 246. For example, interfaces 246 may include what are generally referred to as "Graphical User Interfaces" (often referred to as GUI's) that provide one or more graphical representations to a user, such as user 101, and also be enabled to process user inputs via interfaces 246 using means of selection or input known to those of ordinary skill in the related art that for instance include but are not limited to selections made via a mouse.

Alternatively, one or more embodiments of computer 150 may employ what are referred to as "command line interfaces" (often referred to as CLI's) that provides a text based interaction between computer 150 and user 101. Typically, command line interfaces present output and receive input as lines of text through display devices 245. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces 246 may include one or more GUI's, CLI's or a combination thereof.

It will be understood by those of ordinary skill in the relevant art that there are many possible configurations of the components of computer 150 and that some components that may typically be included in computer 150 are not shown, such as cache memory, a data backup unit, and many other devices. Processor 255 may be a commercially available processor such as an Itanium® or Pentium® processor made by Intel Corporation, a SPARC® processor made by Sun Microsystems, an Athalon™ or Opteron™ processor made by AMD corporation, or it may be one of other processors that are or will become available. Some embodiments of processor 255 may also include what are referred to as Multi-core processors and/or be enabled to employ parallel processing technology in a single or multi-core configuration. For example, a multi-core architecture typically comprises two or more processor "execution cores". In the present example each execution core may perform as an independent processor that enables parallel execution of multiple threads. In addition, those of ordinary skill in the related will appreciate that processor 255 may be configured in what is generally referred to as 32 or 64 bit architectures, or other architectural configurations now known or that may be developed in the future.

Processor 255 executes operating system 260, which may be, for example, a Windows®-type operating system (such as Windows® XP) from the Microsoft Corporation; the Mac OS X operating system from Apple Computer Corp. (such as 7.5 Mac OS X v10.4 "Tiger" or 7.6 Mac OS X v10.5 "Leopard" operating systems); a Unix® or Linux-type operating system available from many vendors or what is referred to as an open source; another or a future operating system; or some combination thereof. Operating system 260 interfaces with firmware and hardware in a well-known manner, and facilitates processor 255 in coordinating and executing the functions of various computer programs that may be written in a variety of programming languages. Operating system 260, typically in cooperation with processor 255, coordinates and executes functions of the other components of computer 150. Operating system 260 also provides scheduling, input-output control, file and data management, memory management, and communication control and related services, all in accordance with known techniques.

System memory 270 may be any of a variety of known or future memory storage devices. Examples include any commonly available random access memory (RAM), magnetic medium such as a resident hard disk or tape, an optical medium such as a read and write compact disc, or other memory storage device. Memory storage devices 281 may be any of a variety of known or future devices, including a compact disk drive, a tape drive, a removable hard disk drive, USB or flash drive, or a diskette drive. Such types of memory storage devices 281 typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 270 and/or the program storage device used in conjunction with memory storage device 281.

In some embodiments, a computer program product is described comprising a computer usable medium having control logic (computer software program, including program code) stored therein. The control logic, when executed by processor 255, causes processor 255 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 275 could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers of input-output controllers 275 could include controllers for any of a variety of known display devices for presenting information to a user, whether a human or a machine, whether local or remote. In the illustrated embodiment, the functional elements of computer 150 communicate with each other via system bus 290. Some of these communications may be accomplished in alternative embodiments using network or other types of remote communications.

Figure 2:
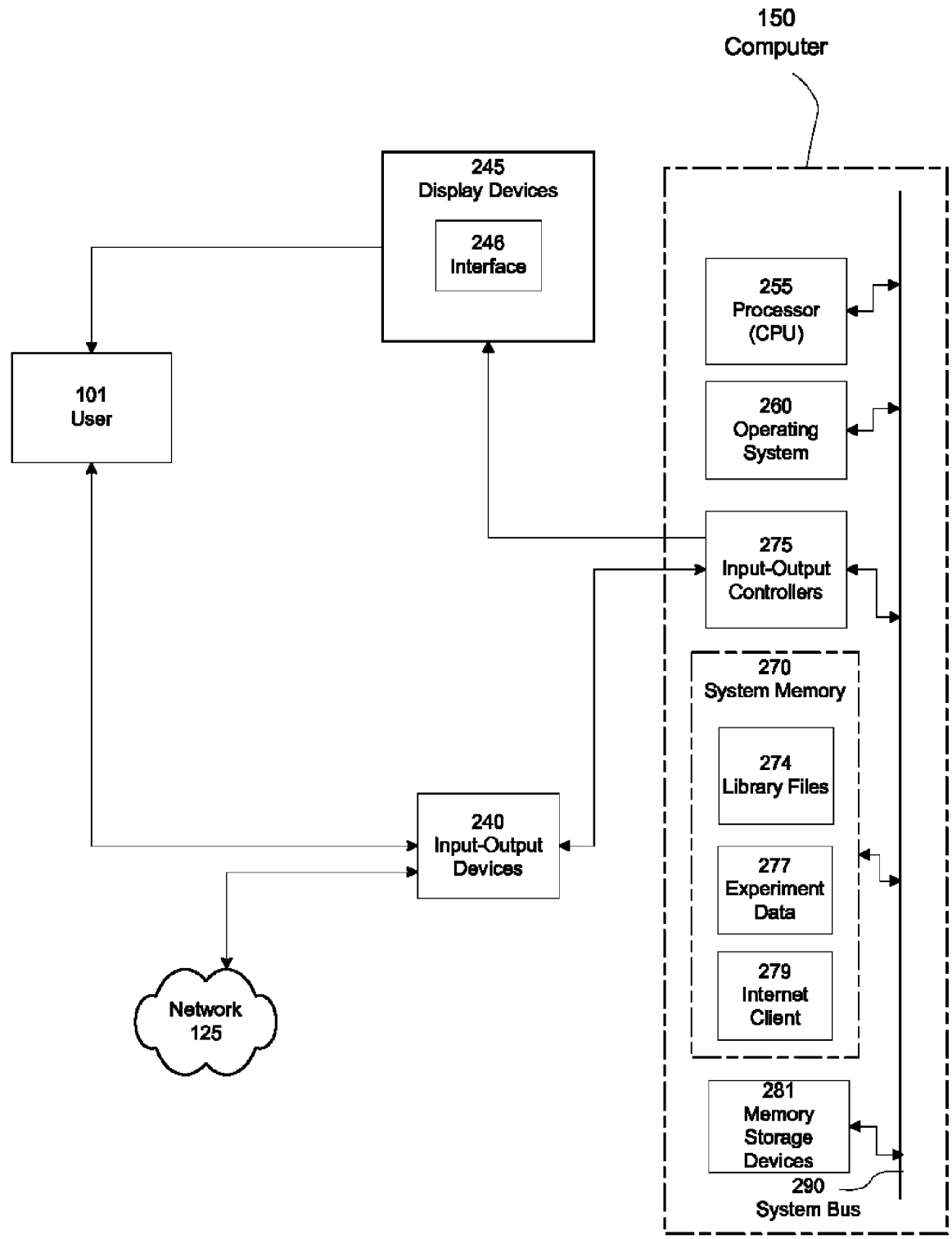
FIG. 2 is a functional block diagram of one embodiment of the computer system of FIG. 1, including a display device and an interface.
Figure 3:
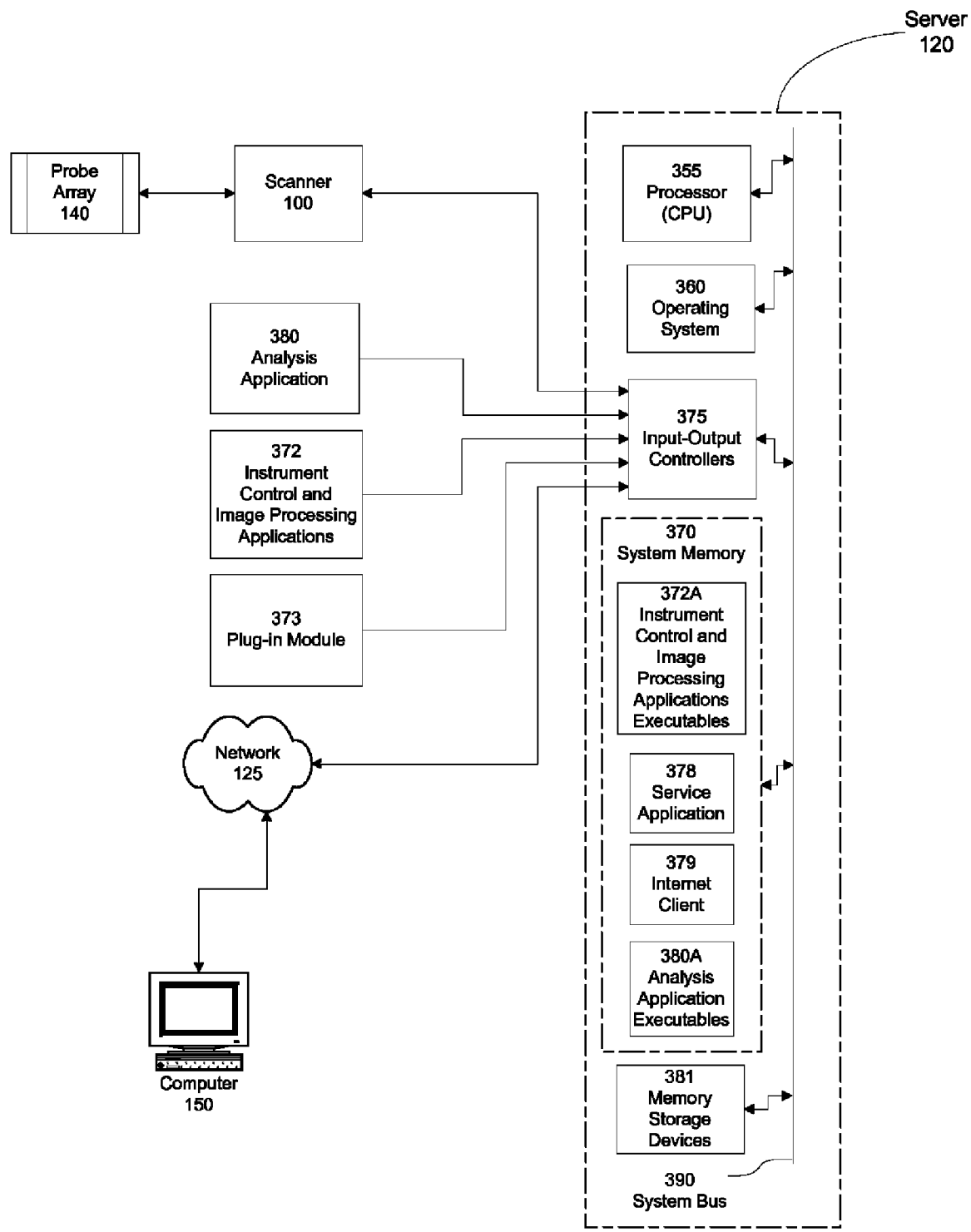
FIG. 3 is a functional block diagram of one embodiment of the server of FIG. 1, including an instrument control and image processing application and an analysis application.

As will be evident to those skilled in the relevant art, an instrument control and image processing application, such as for instance an implementation of instrument control and image processing applications 372 illustrated in FIG. 3, if implemented in software, may be loaded into and executed from system memory 270 and/or memory storage device 281. All or portions of the instrument control and image processing applications may also reside in a read-only memory or similar device of memory storage device 281, such devices not requiring that the instrument control and image processing applications first be loaded through input-output controllers 275. It will be understood by those skilled in the relevant art that the instrument control and image processing applications 372, or portions of it, may be loaded by processor 255 in a known manner into system memory 270, or cache memory (not shown), or both, as advantageous for execution. Also illustrated in FIG. 2 are library files 274, experiment data 277, and internet client 279 stored in system memory 270. For example, experiment data 277 could include data related to one or more experiments or assays such as excitation wavelength ranges, emission wavelength ranges, extinction coefficients and/or associated excitation power level values, or other values associated with one or more fluorescent labels. Additionally, internet client 279 may include an application enabled to accesses a remote service on another computer using a network that may for instance comprise what are generally referred to as "Web Browsers". In the present example some commonly employed web browsers include Netscape® 8.0 available from Netscape Communications Corp., Microsoft® Internet Explorer 6 with SP1 available from Microsoft Corporation, Mozilla Firefox® 1.5 from the Mozilla Corporation, Safari 2.0 from Apple Computer Corp., or other type of web browser currently known in the art or to be developed in the future. Also, in the same or other embodiments internet client 279 may include, or could be an element of, specialized software applications enabled to access remote information via a network such as network 125 such as, for instance, the GeneChip® Data Analysis Software (GDAS) package or Chromosome Copy Number Tool (CNAT) both available from Affymetrix, Inc. of Santa Clara Calif. that are each enabled to access information from remote sources, and in particular probe array annotation information from the NetAffx™ web site hosted on one or more servers provided by Affymetrix, Inc.

Network 125 may include one or more of the many various types of networks well known to those of ordinary skill in the art. For example, network 125 may include a local or wide area network that employs what is commonly referred to as a TCP/IP protocol suite to communicate, that may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

Server 120: FIG. 1 shows a typical configuration of a server computer connected to a workstation computer via a network that is illustrated in further detail in FIG. 3. In some implementations any function ascribed to Server 120 may be carried out by one or more other computers, and/or the functions may be performed in parallel by a group of computers.

Typically, server 120 is a network-server class of computer designed for servicing a number of workstations or other computer platforms over a network. However, server 120 may be any of a variety of types of general-purpose computers such as a personal computer, workstation, main frame computer, or other computer platform now or later developed. Server 120 typically includes known components such as processor 355, operating system 360, system memory 370, memory storage devices 381, and input-output controllers 378. It will be understood by those skilled in the relevant art that there are many possible configurations of the components of server 120 that may typically include cache memory, a data backup unit, and many other devices. Similarly, many hardware and associated software or firmware components may be implemented in a network server. For example, components to implement one or more firewalls to protect data and applications, uninterruptable power supplies, LAN switches, web-server routing software, and many other components. Those of ordinary skill in the art will readily appreciate how these and other conventional components may be implemented.

Processor 355 may include multiple processors; e.g., multiple Intel Xeon™ 3.2 GHz processors. As further examples, the processor may include one or more of a variety of other commercially available processors such as Itanium® 2 64-bit processors or Pentium® processors from Intel, SPARC® processors made by Sun Microsystems, Opteron™ processors from Advanced Micro Devices, or other processors that are or will become available. Processor 355 executes operating system 360, which may be, for example, a Windows®-type operating system (such as Windows® XP Professional (which may include a version of Internet Information Server (IIS))) from the Microsoft Corporation; the Mac OS X Server operating system from Apple Computer Corp.; the Solaris operating system from Sun Microsystems; the Tru64 Unix from Compaq; other Unix® or Linux-type operating systems available from many vendors or open sources; another or a future operating system; or some combination thereof. Some embodiments of processor 355 may also include what are referred to as Multi-core processors and/or be enabled to employ parallel processing technology in a single or multi-core configuration similar to that as described above with respect to processor 255. In addition, those of ordinary skill in the related will appreciate that processor 355 may be configured in what is generally referred to as 32 or 64 bit architectures, or other architectural configurations now known or that may be developed in the future.

Operating system 360 interfaces with firmware and hardware in a well-known manner, and facilitates processor 355 in coordinating and executing the functions of various computer programs that may be written in a variety of programming languages. Operating system 360, typically in cooperation with the processor, coordinates and executes functions of the other components of server 120. Operating system 360 also provides scheduling, input-output control, file and data management, memory management, and communication control and related services, all in accordance with known techniques.

System memory 370 may be any of a variety of known or future memory storage devices. Examples include any commonly available random access memory (RAM), magnetic medium such as a resident hard disk or tape, an optical medium such as a read and write compact disc, or other memory storage device. Memory storage device 381 may be any of a variety of known or future devices, including a compact disk drive, a tape drive, a removable hard disk drive, USB or flash drive, or a diskette drive. Such types of memory storage device typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in the system memory and/or the program storage device used in conjunction with the memory storage device.

In some embodiments, a computer program product is described comprising a computer usable medium having control logic (computer software program, including program code) stored therein. The control logic, when executed by the processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 375 could include any of a variety of known devices for accepting and processing information from a user, whether a human or a machine, whether local or remote. Such devices include, for example, modem cards, network interface cards, sound cards, or other types of controllers for any of a variety of known input or output devices. In the illustrated embodiment, the functional elements of server 120 communicate with each other via system bus 390. Some of these communications may be accomplished in alternative embodiments using network or other types of remote communications.

As will be evident to those skilled in the relevant art, a server application if implemented in software may be loaded into the system memory and/or the memory storage device through one of the input devices, such as instrument control and image processing applications 372 described in greater detail below. All or portions of these loaded elements may also reside in a read-only memory or similar device of the memory storage device, such devices not requiring that the elements first be loaded through the input devices. It will be understood by those skilled in the relevant art that any of the loaded elements, or portions of them, may be loaded by the processor in a known manner into the system memory, or cache memory (not shown), or both, as advantageous for execution.

Instrument control and image processing applications 372: Instrument control and image processing applications 372 may comprise any of a variety of known or future image processing applications. Some examples of known instrument control and image processing applications include the Affymetrix® Microarray Suite, and Affymetrix® GeneChip® Operating Software (hereafter referred to as GCOS) applications. Typically, embodiments of applications 372 may be loaded into system memory 370 and/or memory storage device 381. For example, FIG. 3 provides an example of applications 372 stored for execution in system memory 370 illustrated as instrument control and image processing applications executables 372A. Also, those of ordinary skill in the related art will appreciate that applications 372 may be stored for execution on any compatible computer system, such as computer 150. For example, the described embodiments of applications 372 may, for example, include the Affymetrix® Command-Console™ software application.

Embodiments of applications 372 may provide what is referred to as a modular interface for one or more computers or workstations and one or more servers, as well as one or more instruments. The term "modular" as used herein generally refers to elements that may be integrated to and interact with a core element in order to provide a flexible, updateable, and customizable platform. For example, as will be described in greater detail below applications 372 may comprise a "core" software element enabled to communicate and perform primary functions necessary for any instrument control and image processing application. Such primary functionality may include communication over various network architectures, or data processing functions such as processing raw intensity data into a .dat file. In the present example, modular software elements, such as for instance what may be referred to as a plug-in module, may be interfaced with the core software element to perform more specific or secondary functions, such as for instance functions that are specific to particular instruments. In particular, the specific or secondary functions may include functions customizable for particular applications desired by user 101. Further, integrated modules and the core software element are considered to be a single software application, and referred to as applications 372.

In the presently described implementation, applications 372 may communicate with, and receive instruction or information from, or control one or more elements or processes of one or more servers, one or more workstations, and one or more instruments. Also, embodiments of server 120 or computer 150 with an implementation of applications 372 stored thereon could be located locally or remotely and communicate with one or more additional servers and/or one or more other computers/workstations or instruments.

In some embodiments, applications 372 may be capable of data encryption/decryption functionality. For example, it may be desirable to encrypt data, files, information associated with GUI's 246, or other information that may be transferred over network 125 to one or more remote computers or servers for data security and confidentiality purposes. For example, some embodiments of probe array 140 may be employed for diagnostic purposes where the data may be associated with a patient and/or a diagnosis of a disease or medical condition. It is desirable in many applications to protect the data using encryption for confidentiality of patient information. In addition, one-way encryption technologies may be employed in situations where access should be limited to only selected parties such as a patient and their physician. In the present example, only the selected parties have the key to decrypt or associate the data with the patient. In some applications, the one-way encrypted data may be stored in one or more public databases or repositories where even the curator of the database or repository would be unable to associate the data with the user or otherwise decrypt the information. The described encryption functionality may also have utility in clinical trial applications where it may be desirable to isolate one or more data elements from each other for the purpose of confidentiality and/or removal of experimental biases.

Various embodiments of applications 372 may provide one or more embodiments of interfaces 246 that may include interactive graphical user interfaces that allows user 101 to make selections based upon information presented in an embodiment of interface 246. Those of ordinary skill will recognize that embodiments of interface 246 may include GUI's as described above coded in various language formats such as an HTML, XHTML, XML, javascript, Jscript, or other language known to those of ordinary skill in the art used for the creation or enhancement of "Web Pages" viewable and compatible with internet client 279. For example, internet client 279 may include various internet browsers such as Microsoft Internet Explorer, Netscape Navigator, Mozilla Firefox, Apple Safari, or other browsers known in the art. Applications of GUI's viewable via one or more browsers may allow user 101 complete remote access to data, management, and registration functions without any other specialized software elements. Applications 372 may provide one or more implementations of interactive GUI's that allow user 101 to select from a variety of options including data selection, experiment parameters, calibration values, and probe array information within the access to data, management, and registration functions.

In some embodiments, applications 372 may be capable of running on operating systems in a non-English format, where applications 372 can accept input from user 101 via interface 246 in various non-English language formats such as Chinese, French, Spanish etc., and output information to user 101 in the same or other desired language output. For example, applications 372 may present information to user 101 in various implementations of a GUI in a language output desired by user 101, and similarly receive input from user 101 in the desired language. In the present example, applications 372 is internationalized such that it is capable of interpreting the input from user 101 in the desired language where the input is acceptable input with respect to the functions and capabilities of applications 372.

Embodiments of applications 372 also include instrument control features, where the control functions of individual types or specific instruments such as scanner 100, an autoloader, or a fluid processing system may be organized as plug-in type modules 373 to applications 372. For example, each plug-in module 373 may be a separate component and may provide definition of the instrument control features to applications 372. As described above, each plug-in module 373 is functionally integrated with applications 372 when stored in system memory 270 and thus reference to applications 372 includes any embodiments of integrated plug-in modules 373. In the present example, each instrument may have one or more associated embodiments of plug-in module 373 that for instance may be specific to model of instrument, revision of instrument firmware or scripts, number and/or configuration of instrument embodiment, etc. Further, multiple embodiments of plug-in module 373 for the same instrument such as scanner 100 may be stored in system memory 270 for use by applications 372, where user 101 may select the desired embodiment of module to employ, or alternatively such a selection of module may be defined by data encoded directly in a machine readable identifier or indirectly via the array file, library files, experiments files and so on.

The instrument control features may include the control of one or more elements of one or more instruments that could, for instance, include elements of a hybridization device, a fluid processing instrument, an autoloader, or scanner 100. The instrument control features may also be capable of receiving information from the one or more instruments that could include experiment or instrument status, process steps, or other relevant information. The instrument control features could, for example, be under the control of or an element of the interface of applications 372. In some embodiments, a user may input desired control commands and/or receive the instrument control information via one of interfaces 246. Additional examples of instrument control via a GUI or other interface is provided in U.S. patent application Ser. No. 10/764,663, titled "System, Method and Computer Software Product for Instrument Control, Data Acquisition, Analysis, Management and Storage", filed Jan. 26, 2004, which is hereby incorporated by reference herein in its entirety for all purposes.

In some embodiments, applications 372 may employ what may referred to as an "array file" that comprises data employed for various instruments, processing functions of images by applications 372, or other relevant information. Generally it is desirable to consolidate elements of data or metadata related to an embodiment of probe array 140, experiment, user, or some combination thereof, to a single file that is not duplicated (i.e. as embodiments of .dat file may be in certain applications), where duplication may sometimes be a source of error. The term "metadata" as used herein generally refers to data about data. It may also be desirable in some embodiments to restrict or prohibit the ability to overwrite data in the array file. Preferentially, new information may be appended to the array file rather than deleting or overwriting information, providing the benefit of traceability and data integrity (i.e. as may be required by some regulatory agencies). For example, an array file may be associated with one or more implementations of an embodiment of probe array 140, where the array file acts to unify data across a set of probe arrays 140. The array file may be created by applications 372 via a registration process, where user 101 inputs data into applications 372 via one or more of interfaces 246. In the present example, the array file may be associated by user 101 with a custom identifier that could include a machine readable identifier such as the machine readable identifiers described in greater detail below.

Alternatively, applications 372 may create an array file and automatically associate the array file with a machine readable identifier that identifies an embodiment of probe array 140 (i.e. relationship between the machine readable identifier and probe array 140 may be assigned by a manufacturer). Applications 372 may employ various data elements for the creation or update of the array file from one or more library files, such as library files 274 or other library files.

Also in the same or alternative embodiments, the array file may comprise pointers to one or more additional data files comprising data related to an associated embodiment of probe array 140. For example, the manufacturer of probe array 140 or other user may provide library files 274 or other files that define characteristics such as probe identity; dimension and positional location (i.e. with respect to some fiducial reference or coordinate system) of the active area of probe array 140; various experimental parameters; instrument control parameters; or other types of useful information. In addition, the array file may also contain one or more metadata elements that could include one or more of a unique identifier for the array file, human readable form of a machine readable identifier, or other metadata elements. In addition, applications 372 may store data (i.e. as metadata, or stored data) that includes sample identifiers, array names, user parameters, event logs that may for instance include a value identifying the number of times an array has been scanned, relationship histories such as for instance the relationship between each .cel file and the one or more .dat files that were employed to generate the .cel file, and other types of data useful in for processing and data management.

For example, user 101 and/or automated data input devices or programs (not shown) may provide data related to the design or conduct of experiments. User 101 may specify an Affymetrix catalogue or custom chip type (e.g., Human Genome U133 plus 2.0 chip) either by selecting from a predetermined list presented in one or more of interfaces 246 or by scanning a bar code, Radio Frequency Identification (RFID), magnetic strip, or other means of electronic identification related to probe array 140 to read its type, part no., array identifier, etc. Applications 372 may associate the chip type, part no., array identifier with various scanning parameters stored in data tables or library files, such as library files 274 of computer 150, including the area of probe array 140 that is to be scanned, the location of chrome elements or other features on probe array 140 used for auto-focusing, the wavelength or intensity/power of excitation light to be used in reading the chip, and so on. Also, some embodiments of applications 372 may encode array files in a binary type format that may minimize the possibility of data corruption. However, applications 372 may be further enabled to export an array file in a number of different formats.

Also continuing the example above, some embodiments of RFID tags associated with embodiments of probe array 140 may be capable of "data logging" functionality where, for instance, each RFID tag or label may actively measure and record parameters of interest. In the present example, such parameters of interest may include environmental conditions such as temperature and/or humidity that the implementation of probe array 140 may have been exposed to. In the present example, user 101 may be interested in the environmental conditions because the biological integrity of some embodiments of probe array 140 may be affected by exposure to fluctuations of the environment. In some embodiments, applications 372 may extract the recorded environmental information from the RFID tag or label and store it in the array file, or some other file that has a pointer to or from the array file. In the same or alternative embodiments, applications 372 may monitor the environmental conditions exposed to the probe array in real time, where applications 372 may regularly monitor information provided by one or more RFID tags simultaneously. Applications 372 may further analyze and employ such information for quality control purposes, for data normalization, or other purposes known in the related art. Some examples of RFID embodiments capable to recording environmental parameters include the ThermAssureRF™ RFID sensor available from Evidencia LLP of Memphis Term., or the Tempsens™ RFID datalogging label available from Exago Pty Ltd. of Australia.

Also, in the same or alternative embodiments, applications 372 may generate or access what may be referred to as a "plate" file. The plate file may encode one or more data elements such as pointers to one or more array files, and preferably may include pointers to a plurality of array files.

In some embodiments, raw image data is acquired from scanner 100 and operated upon by applications 372 to generate intermediate results. For example, raw intensity data acquired from scanner 100 may be directed to a .dat file generator and written to data files (*.dat) that comprises an intensity value for each pixel of data acquired from a scan of an embodiment of probe array 140. In the same or alternative embodiments it may be advantageous to scan sub areas (that may be referred to as sub arrays) of probe array 140 where the detected signal for each sub area scanned may be written to an individual embodiment of a .dat file. Continuing with the present example, applications 372 may also encode a unique identifier for each .dat file as well as a pointer to an associated embodiment of an array file as metadata into each .dat file generated. The term "pointer" as used herein generally refers to a programming language datatype, variable, or data object that references another data object, datatype, variable, etc. using a memory address or identifier of the referenced element in a memory storage device such as in system memory 270. In some embodiments the pointers comprise the unique identifiers of the files that are the subject of the pointing, such as for instance the pointer in a .dat file comprises the unique identifier of the array file. Additional examples of the generation and image processing of sub arrays is described in U.S. patent application Ser. No. 11/289,975, titled "System, Method, and Product for Analyzing Images Comprising Small Feature Sizes", filed Nov. 30, 2005, which is hereby incorporated by reference herein in its entirety for all purpose.

Also, applications 372 may also include a .cel file generator that may produce one or more .cel files (*.cel) by processing each .dat file. Alternatively, some embodiments of .cel file generator may produce a single .cel file from processing multiple .dat files such as with the example of processing multiple sub-arrays described above. Similar to the .dat file described above each embodiment of .cel file may also include one or more metadata elements. For example, applications 372 may encode a unique identifier for each .cel file as well as a pointer to an associated array file and/or the one or more .dat files used to produce the .cel file.

Each .cel file contains, for each probe feature scanned by scanner 100, a single value representative of the intensities of pixels measured by scanner 100 for that probe. For example, this value may include a measure of the abundance of tagged mRNA's present in the target that hybridized to the corresponding probe. Many such mRNA's may be present in each probe, as a probe on a GeneChip® probe array may include, for example, millions of oligonucleotides designed to detect the mRNA's. Alternatively, the value may include a measure related to the sequence composition of DNA or other nucleic acid detected by the probes of a GeneChip® probe array. As described above, applications 372 receives image data derived from probe array 140 using scanner 100 and generates a .dat file that is then processed by applications 372 to produce a .cel intensity file, where applications 372 may utilize information from an array file in the image processing function. For instance, the .cel file generator may perform what is referred to as grid placement methods on the image data in each .dat file using data elements such as dimension information to determine and define the positional location of probe features in the image. Typically, the .cel file generator associates what may be referred to as a grid with the image data in a .dat file for the purpose of determining the positional relationship of probe features in the image with the known positions and identities of the probe features. The accurate registration of the grid with the image is important for the accuracy of the information in the resulting .cel file. Also, some embodiments of .cel file generator may provide user 101 with a graphical representation of a grid aligned to image data from a selected .dat file in an implementation of interface 246 comprising a GUI, and further enable user 101 to manually refine the position of the grid placement using methods commonly employed such as placing a cursor over the grid, selecting such as by holding down a button on a mouse, and dragging the grid to a preferred positional relationship with the image. Applications 372 may then perform methods sometimes referred to as "feature extraction" to assign a value of intensity for each probe represented in the image as an area defined by the boundary lines of the grid. Examples of grid registration, methods of positional refinement, and feature extraction are described in U.S. Pat. Nos. 6,090,555; 6,611, 767; 6,829,376, and U.S. patent application Ser. Nos. 10/391, 882, and 10/197,369, each of which is hereby incorporated by reference herein in it's entirety for all purposes.

As noted, another file that may be generated by applications 372 is a .chp file using a .chp file generator. For example, each .chp file is derived from analysis of a .cel file combined in some cases with information derived from an array file, other lab data and/or library files 274 that specify details regarding the sequences and locations of probes and controls.

In some embodiments, a machine readable identifier associated with probe array 140 may indicate the library file directly or indirectly via one or more identifiers in the array file, to employ for identification of the probes and their positional locations. The resulting data stored in the .chp file includes degrees of hybridization, absolute and/or differential (over two or more experiments) expression, genotype comparisons, detection of polymorphisms and mutations, and other analytical results.

In some alternative embodiments, user 101 may prefer to employ different applications to process data such as an independent analysis application. An embodiment of an analysis application is illustrated in FIG. 3 as analysis application 380, and also illustrated as stored for execution in system memory 370 as analysis application executables 380A. Embodiments of analysis application 380 may comprise any of a variety of known or probe array analysis applications, and particularly analysis applications specialized for use with particular embodiments of probe array 140 such as those designed for certain genotyping or expression applications. For example, one such embodiment of analysis application 380 may include elements that are specialized for analysis of data from embodiments of probe array 140 comprising probes that interrogate exon regions.

Various embodiments of analysis application 380 may exist such as applications developed by a probe array manufacturer for specialized embodiments of probe array 140, commercial third party software applications, open source applications, or other applications known in the art for specific analysis of data from probe arrays 140. Some examples of known genotyping analysis applications include the Affymetrix® GeneChip® Data Analysis System (GDAS), Affymetrix® GeneChip® Genotyping Analysis Software (GTYPE), Affymetrix® GeneChip® Targeted Genotyping Analysis Software (GTGS), and Affymetrix® GeneChip® Sequence Analysis Software (GSEQ) applications. Additional examples of genotyping analysis applications may be found in U.S. patent application Ser. Nos. 10/657,481; 10/986,963; and 11/157,768; each of which is hereby incorporated by reference herein in it's entirety for all purposes. Typically, embodiments of analysis applications may be loaded into system memory 370 and/or memory storage device 381.

Some embodiments of analysis applications include executable code being stored in system memory 370. Applications 372 may be enabled to export .cel files, .dat files, or other files to an analysis application or enable access to such files on computer 150 by the analysis application. Import and/or export functionality for compatibility with specific systems or applications may be enabled by one or more integrated modules as described above with respect to plug-in modules. For example, an analysis application may be capable of performing specialized analysis of processed intensity data, such as the data in a .cel file. In the present example, user 101 may desire to process data associated with a plurality of implementations of probe array 140 and therefore the analysis application would receive a .cel file associated with each probe array for processing. In the present example, applications 372 forwards the appropriate files in response to queries or requests from the analysis application.

In the same or alternative examples, user 101 and/or the third party developers may employ what are referred to as software development kits that enable programmatic access into file formats, or the structure of applications 372. Therefore, developers of other software applications such as the described analysis application may integrate with and seamlessly add functionally to or utilize data from applications 372 that provides user 101 with a wide range of application and processing capability. Additional examples of software development kits associated with software or data related to probe arrays are described in U.S. Pat. No. 6,954,699, and U.S. application Ser. Nos. 10/764,663 and 11/215,900, each of which is hereby incorporated by reference herein in its entirety for all purposes.

Additional examples of .cel and .chp files are described with respect to the Affymetrix GeneChip® Operating Software or Affymetrix® Microarray Suite (as described, for example, in U.S. patent application Ser. Nos. 10/219,882, and 10/764,663, both of which are hereby incorporated herein by reference in their entireties for all purposes). For convenience, the term "file" often is used herein to refer to data generated or used by applications 372 and executable counterparts of other applications such as analysis application 380, where the data is written according a format such as the described .dat, .cel, and .chp formats. Further, the data files may also be used as input for applications 372 or other software capable of reading the format of the file.

Those of ordinary skill in the related art will appreciate that one or more operations of applications 372 may be performed by software or firmware associated with various instruments. For example, scanner 100 could include a computer that may include a firmware component that performs or controls one or more operations associated with scanner 100.

Yet another example of instrument control and image processing applications is described in U.S. patent application Ser. No. 11/279,068, titled "System, Method and Computer Product for Simplified Instrument Control and File Management", filed Apr. 7, 2006, which is hereby incorporated by reference herein in its entirety for all purposes.

Figure 4:
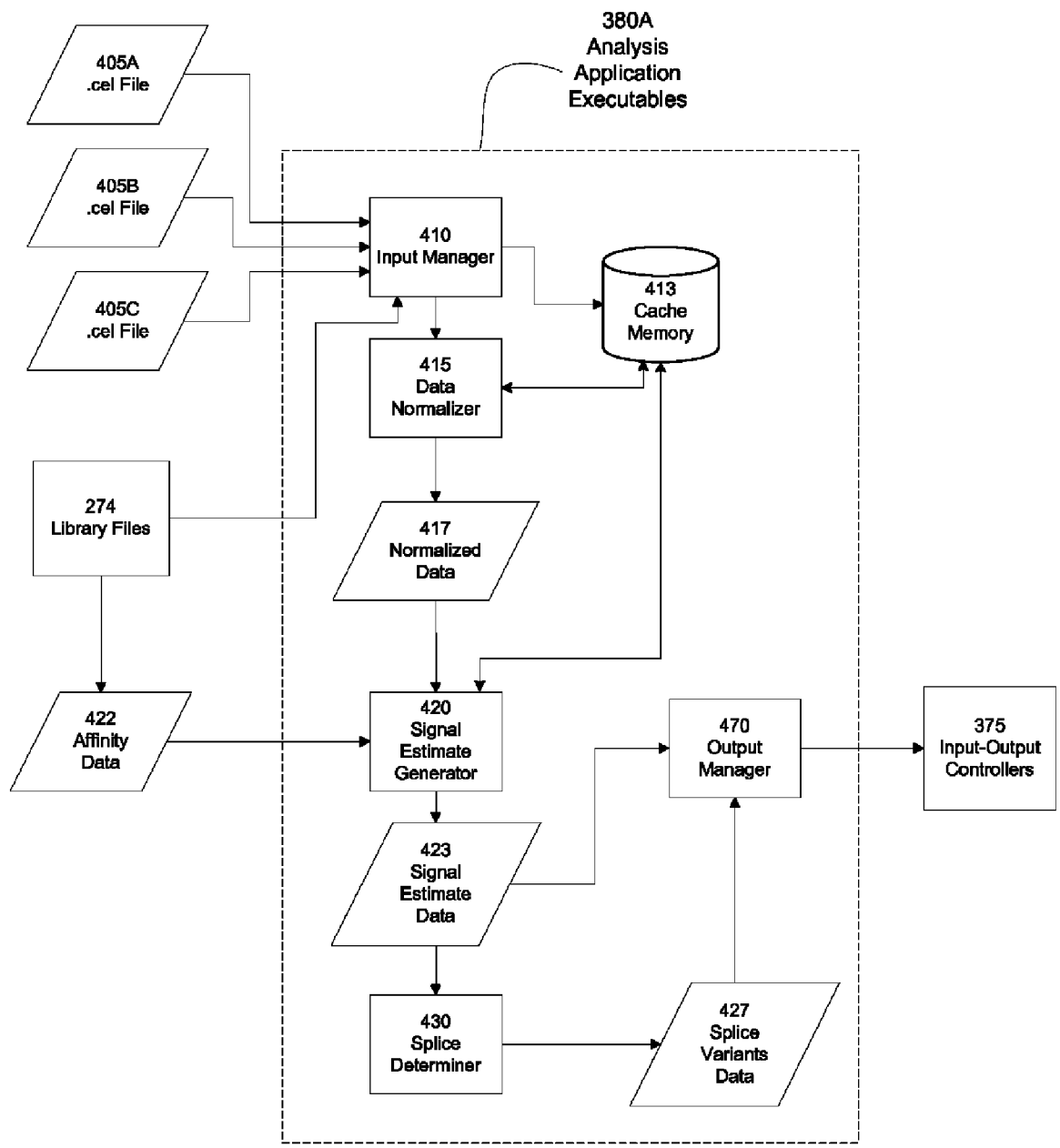
FIG. 4 is a functional block diagram of one embodiment of the analysis application of FIG. 3.

Analysis Application 380 An illustrative example of analysis application 380 is provided in FIG. 3, and in greater detail in FIG. 4. Some embodiments of analysis application 380 serves as a stand-alone application for processing intermediate results such as, for instance, one or more .cel files generated by instrument control and image processing applications 372 as described above. For example, analysis application 380 may comprise elements or tools especially suited for analysis of specialized or emerging applications of probe arrays 140 as described above, such as for example the exon probe arrays. In the present example, probe array 140 may include probe sets, where each probe set is directed to a known or predicted "gene", or region of interest that may be associated with a function. Each probe set includes one or more probes directed to each known and/or predicted exon region of the nucleic acid sequence associated with the gene or functional region. Analysis application 380 may be specialized to analyze intensity values for each probe and provide results including the identification of biological events such as one or more alternative splicing events associated with the gene or functional region that occur in biological contexts.

In general, Embodiments of analysis application 380 are organized to handle and manage the processing steps and data in an efficient manner, where application 380 may be particularly suited to analyze large volumes of data associated with multiple data sets. Similar to processing application 372 described above, embodiments of analysis application 380 may be implemented as functional program modules that provide design flexibility as well as enabling an efficient means to update or means to improve analysis applications 380.

Application 380 may implement updates and improvements by adding, removing, and/or updating modules as opposed to reworking the entire software application that often requires a new release that replaces a former version. In other words, application 380 is a more flexible application that allows user 101 the ability to dynamically update the software without having to install a new application. Also, some embodiments of analysis application 380 may be structured to comprise a set of modules amenable to interaction with a well defined Applications Programming Interface (API). For example, the modular architecture of analysis application 380 provides user 101 with the ability to customize the application using the API's to suit the individual needs of user 101. In the present example, user 101 may desire to optimize one or more of the methods, workflow or process steps, or tools to best accommodate the particular conditions or aspects of the analysis. Additional examples of APIs for programmatic access to software or data structure/files associated with biological probe arrays may be found in U.S. Pat. No. 6,954,699, titled "System and Method for Programmatic Access to Biological Probe Array Data", incorporated by reference above.

Further, the architecture of analysis application 380 allows for platform independence and scalability. For example, user 101 may wish to employ what may be referred to in the art as a linux cluster or other high performance computing environment in order to process large amounts of information. Alternatively, user 101 may not have the need for such large scale computing and the costs associated with high performance computing environments and choose a smaller scale computing environment, such as for instance computer 150. In the present example, user 101 may choose the hardware application and operating software platforms that best suits their needs.

Modules implemented by analysis application 380 may be written in an object-oriented programming language such as for instance C, C++, Java, or other high level or object-oriented language currently used in the art or that may be developed in the future. For example, in some implementations the modules of analysis application 380 written using one or more of the languages described above may be integrated using other tools know in the art such as for instance what is referred to as "Simplified Wrapper and Interface Generator" (SWIG) tool that employs "scripting languages" such as Perl, PHP, Python, Tcl, Ruby and PHP to functionally join software elements.

The modules employed by analysis application 380 confer functionality for processing .cel files 405 that result in signal estimations and identification of biological events that comprise alternatively spliced variation associated with the genes or functional regions represented by the intensity values. For example, the functionality may include one or more of data handling functions, normalization functions, signal estimation functions, gene-level or splice variant estimations, annotation functions, and display functions.

Some embodiments of analysis applications 380 may include one or more modules comprising tools or elements to extract or receive data from an external source. The term "external" as used herein generally refers to a source that is external to analysis application 380 but may reside in the same memory or processing unit or alternatively in a memory or processing unit associated with a computer that is remotely located with respect to the computer that executes applications 380. For example, applications 380 may employ a module for importing implementations of .cel 405 from applications 372 into application 380 for processing. In the present example, each implementation of .cel 405 imported may be selected by user 101, or identified in an experiment file.

Also embodiments of analysis application 380 may include one or more modules that confer normalization functionality for data contained within .cel files 405. The term "normalize" as used herein generally refers to processing data to reduce or remove effects caused by what may be referred to as noise. For instance normalization may be employed to remove certain biases, or spurious information that is not directly related to what may be considered real data representative of the actual biological event. In some applications, normalization methods may be employed to improve the comparability of data between different data sets such as intensity data represented in different .cel files. Applications 380 may be capable of applying different normalization methods that may again be selected by user 101 or retrieved from a data file.

Various types of normalization methods may be employed by application 380. For example, the normalization functions of analysis application 380 may include what may be referred to by those of ordinary skill in the related art as "Global linear scaling based on median intensity", or "Quantile Normalization" (as described by B. M. Bolstad, R. A Irizarry, M. Åstrand, and T. P. Speed Bioinformatics 2003 vol. 19, no. 2: 185-193, which is hereby incorporated by reference herein in it's entirety for all purposes) methods. In the present example, the global linear scaling method typically includes the calculation and application of a scaling factor for each .cel file dataset using the median intensity values of each dataset. Also, the quantile normalization method may include ranking the intensity values representing each probe within each .cel file, and normalizing the values by rank by taking the average of the intensity values for the ranks in each .cel file. It will also be appreciated by those of ordinary skill in the art that both the global linear scaling and quantile normalization methods are computationally and memory intensive and may not be the most efficient means to normalize .cel files 405.

Another method of normalization employed by application 380 may include what may be referred to as "sketch normalization". For example, sketch normalization employs a similar mathematical concept as quantile normalization but achieves the results in a significantly more efficient manner that reduces computational time and resources. In the present example, sketch normalization assumes that the distribution of intensity values in each .cel file 405 is relatively uniform and therefore a subset of intensity values effectively represents the characteristics of all intensity values. Thus, as opposed to performing calculations using every value in the entire set of data, the sketch normalization method employs a representative subset of intensity values to perform the calculations. For instance, the sketch normalization method may employ an intensity value associated with one probe from every probe set represented in a .cel file as a representative set of intensity values, although it will be appreciated that this example is provided for the purposes of example and should not be considered as limiting. Application 380 may store the sketch subset as a file in library files 274, cache memory 413, or other storage element previously described, for later use by analysis application 380.

Embodiments that employ the sketch normalization method typically do not need to perform the step of ranking described for quantile normalization because the representative subset represents the distribution of intensities and analysis application 380 may interpolate additional intensity values from the representative sub set. Application 380 may then apply the interpolated distribution as it would for quantile normalization to generate normalized .cel file 417, or alternatively normalize .cel files dynamically as a step in other analysis processes.

Also, analysis application 380 may apply the sketch normalization method to smaller units, such as probe sets that provides the further computational advantage of analyzing small datasets. Thus, sketch normalization eliminates the need to open and process all data associated with a .cel file, substantially reduces the number of computations made for each .cel file 405, as well as a reduces the number of estimated parameters stored for each analysis.

Application 380 may also include what may employ one or more modules that confer what may be referred to as "signal estimation" functionality. The term "signal estimation" as used herein generally refers to a value that is a representation of what the true signal is. In other words, what the actual signal should be with noise and experimental artifacts removed. Analysis application 380 may employ various methods for signal estimation that includes but are not limited to what may be referred to as the Probe Logarithmic Intensity Error Estimate (referred to as PLIER) as described by Hubbell, *PLIER Whitepaper*, available from the web site hosted by Affymetrix, Inc.; and further described in Thompson et al., *Use of a mixed tissue RNA design for performance assessments on multiple microarray formats*, Nucleic Acids Research 2005 33(22):e187, which is hereby incorporated by reference herein in it's entirety for all purposes; and what may be referred to as Robust Multi-Array Average (referred to as RMA) as described by Irizarry et al., *Summaries of Affymetrix GeneChip probe level data*, Nucleic Acids Research, 2003 31(4):e15, which is hereby incorporated by reference herein in it's entirety for all purposes. For example, analysis application 380 may employ the PLIER algorithm to generate a probe-level estimation of signal intensity using an affinity value that represents a probes affinity to bind to its target molecule.

Even further analysis application 380 may employ one or more modules that confer functionality that provide estimations of alternative splice variant identification. As described above the modules may employ a variety of methods to provide such functionality. One such method may include what may be referred to as a deconvolution algorithm as described by Wang et al. in a paper titled *Gene Structure-Based Splice Variant Deconvolution Using a Microarray Platform*, Bioinformatics 2003 19(Suppl 1):i315-i322, which is hereby incorporated by reference herein in it's entirety for all purposes. The method employs a model-based approach to estimate the relative concentration of splice variants for each particular gene. For example, the deconvolution algorithm may use probe intensity values and gene structure information that specifies the exon composition and arrangement that are interrogated by each particular probe. In the present example, the relationship between the intensity values for each probe of a gene in question and the gene structure information is evaluated and the relative amounts of splice variants is determined as well as a measure of affinity for the target molecule is associated with each probe. The method includes a model for probe-level intensities $x_{h,i,j,k}$ that include an extra multiplicative term denoting affinity $a_{h,i,k}$ of probe h of exon i of gene k in tissue j.

$$x_{h,i,j,k} = a_{h,i,k} \alpha_{i,k} p_{i,j,k} g_{j,k} + \epsilon_{h,i,j,k} \quad \text{equation (1)}$$

The method implements an iterative Maximum Likelihood Estimation method that includes $p_{i,j,k}$ to estimate parameters. In the present example, for any one gene k, the relative ratios of $p_{i,j,k}$ across tissues j represent relative concentration estimates of exons. Therefore, analysis application 380 determines that alternative splicing has occurred if the relative ratios deviate from each other in a statistically significant way.

Another method for determining alternative splice variants may be referred to as the pattern-based correlation (PAC) method as described in a whitepaper titled *Alternative Tran-* script *Analysis Methods for Exon Arrays* available from the web site hosted by Affymetrix, Inc. For example, the PAC method may correlate the pattern of intensity values associated with exon probes to determine in the gene is alternatively spliced or not. The PAC method uses the assumption that in the absence of splicing, probe intensities associated with expressed exons follows gene expression across samples using the following model:

$$e_{i,j,k} = n_{i,k} g_{j,k} \quad \text{equation (2)}$$

Where $e_{i,j,k}$ is the signal of the i-th exon of the j-th sample of the k-th gene; $g_{j,k}$ is the signal of the k- the gene in the j-th sample; and $n_{i,k}$ is the ratio of exon i signal to its gene signal.

The method applies a robust measure of gene signal and correlates the signal associated with each exon with this signal. A low correlation is an indication of alternative splicing.

Yet another method may include what is referred to as a method called Analysis of Splice Variation (i.e. ANOSVA) as described by Cline et al., *ANOSVA: a statistical method for detecting splice variation from expression data*, Bioinformatics 2005 21(Suppl 1):i107-i115, which is hereby incorporated by reference herein in it's entirety for all purposes. For example, the ANOSVA method requires no transcript information, so can be applied when the level of annotation is poor. In other words the method can be applied when existing knowledge of the possible transcripts is incomplete. In the present example, the method applies a classical ANOVA statistical model to identify the sort of grouping in the residuals. For each gene or functional region the application 380 takes the log of all probe intensities associated with each .cel file 405 in a study. The method assumes that each probe is associated with exactly one probe set, and each experiment is associated with exactly one set of replicated experiments, or one experimental condition, and shall extend the labeling to include probe set and experiment set. The method also assumes that there are multiple probe sets per gene, measuring different exon features.

The ANOVA model fits the observed data to a linear model of one or more input quantities (factors), and can be used to estimate the importance of each factor to the model. For two-way ANOVA with replication, each observation $y_{ijkl}$ is modeled by a combination of two factors, as follows:

$$y_{ijkl} = \mu + \alpha_i + \beta_j + \gamma_{ij} + \text{error} \quad \text{equation (3)}$$

In an expression analysis framework, $y_{ijkl}$ represents the observed log intensity of probe k of probe set i, measured in experiment j of experiment set l. The two factors are probe set (indexed by i) and experiment set (indexed by j). The term $\mu$ is an intercept, and represents a baseline intensity level for all probes in all experiments. The term $\alpha_i$ represents the linear contribution to y from probe set i, and is analogous to the average probe affinity $\phi_i$ of each probe set. The term "affinity" as used herein generally refers to a probe ability to hybridize with a molecule having complementary sequence characteristics, where a probe that hybridizes efficiently with the target molecule has a high affinity. The term $\beta_j$ represents the linear contribution to y from the second factor and can be though of as the average target concentration $\theta_j$ for each experiment set. The term "target concentration" as used herein generally refers to the concentration of a target molecule in a sample typically employed in an experiment.

The term $\gamma_{ij}$ describes the interaction effect for each combination of the two factors. Statistically, an interaction effect represents information in the combination of the factors not represented by the factors independently. Stated more simply, it represents additional signal applied to every combination of the two factors to make the model fit the data. The ANOVA framework is used to test the null hypothesis that the interaction terms are all zero against the alternative that one or more of the interaction terms is nonzero. Rejection of the null hypothesis indicates that it is unlikely the observed data are consistent with a model with no interaction terms. In analysis, rejection of this null indicates that the probe intensities cannot be modeled with one target concentration term per experiment and one affinity term per probe set, which indicates alternative splicing. Further, in some embodiments to identify genes with significant splice variation, we assess the significance of each interaction coefficient $\gamma_{ij}$ for each probe set i and experiment set j. We record the smallest P value, and interpret this P value as a measure of confidence that the gene exhibits alternative splicing.

An assessment of the significance of each interaction coefficient $\gamma_{ij}$ may be generated using a t-test, where the numerator is the coefficient (and is technically the difference between the coefficient and zero), the denominator is the standard error of the coefficient as derived in the linear modeling process. The number of degrees of freedom is N–v–1, where N is the sample size and v is the number of terms in the statistical model. The method is employed by application 380 to identify genes with significant splice variation, by assessing the significance of each interaction coefficient $\gamma_{ij}$ for each probe set i and experiment set j using the P-value result of the t-test For instance, a small P value is interpreted as a measure of confidence that the gene exhibits alternative splicing.

Additional examples of Analysis of Variance (ANOVA) type methods for identifying alternative splice variants from probe intensity data is described in U.S. Provisional Patent Application Ser. No. 60/695,814, titled "Methods and Systems for Detection of Alternative Splice", filed Jun. 29, 2005, which is hereby incorporated by reference herein in it's entirety for all purposes.

As described above, embodiments of analysis application 380 includes one or more modules that provide a means to process data from implementations of probe array 140 in a computationally and memory efficient manner. In addition, analysis application may include functionality that allows application 380 to process multiple .cel files 405 each associated with an implementation of probe array 140 efficiently to reduce computation time and resource usage. For example, those of ordinary skill in the related art will appreciate that .cel files 405 can be quite large, some comprising intensity values representing over 5 million probe features where opening a plurality of files 405 simultaneously for processing would utilize a substantial amount of computer memory and compromise processing efficiency. In some applications, user 101 may not be interested in processing all data contained in the multiple files, such as the .cel files represented in FIG. 4 as files 405A, 405B, and 405C. For instance user 101 may only be interested in processing data for a particular subset of probe sets and thus processing all of the data from each of the files would be an inefficient use of time and resources. In applications where user 101 may want to process all data from each of files 405, it may still be advantageous to process subsets of data as described above in a parallel fashion, such as for example, different subsets could be parsed out to multiple processors. An example of a parallel processing system includes what is referred to as a compute farm (or a Linux compute farm as a specific example). Each computer (sometimes referred to as a node) of the compute farm may process the data in a subset assigned by application 380 in parallel with other nodes and return the processed results to application 380 to be combined. Thus it should be apparent that parallel processing reduces the amount of time to process the data with respect to the time required to process in a serial fashion on a single processor.

Figure 5:
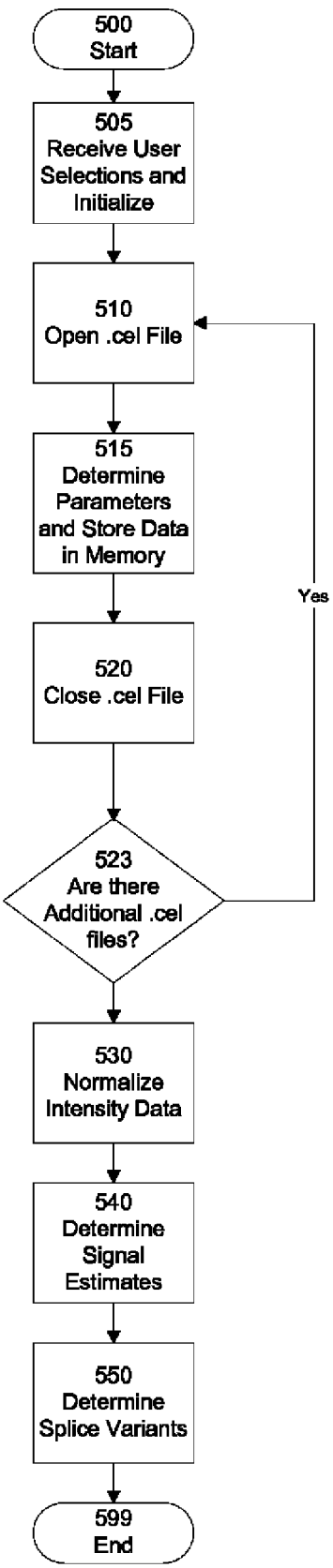
FIG. 5 is a functional block diagram of one embodiment of a method for computational and memory efficient data processing.

FIG. 5 provides an illustrative example of how analysis application 380 handles and processes intensity data using some or all of the functionality conferred by the modules as described above. For example, analysis application 380 may operate by creating what are referred to as data objects for handling and processing data. The data objects provide the advantage of storing in memory only necessary information for the processing functionality to be performed such as intensity data and other parameter information. As opposed to opening large files that take up large segments of memory where the file contains additional information that is not necessary for the processing operations. In addition, it is more efficient from a memory usage perspective for analysis application 380 to only have a single .cel file open at any given time. For example, analysis application 380 may create a data object, open and read information from an embodiment of .cel file 405, store only needed information in the data object, and close the .cel file. In the present example, analysis application 380 may iteratively repeat the process for each embodiment on .cel file 405 to be analyzed. In some embodiments, analysis application may perform some or all of the processing functionality on the data in the data object before opening and reading data from another .cel file.

Also the data objects may be organized as classes, where each class has a specific function. For instance one such class may be employed for representing subsets of intensity data from a .cel file in memory. Also, certain classes may be related to each other where one class may utilize some or all of the functionality of another related class.

Input manager 410 of analysis application 380 may initialize a workflow process creating the data objects, where the initialization and specification of the objects are responsive to the user's indication of methods to implement and the data to be acted upon. For example, input manager 410 may call one or more software modules that include functionality for creating the one or more objects and populate them with the appropriate information, where one or more of the objects may also be linked to create what may be referred to as a data transformation path or stream. Step 505 of FIG. 5 illustrates an example where input manager 410 receives the user selections of intensity data to analyze and functional methods to perform. Manager 410 identifies one or more .cel files 405 selected by user 101, such as one or more of .cel file 405A, .cel file 405B, and .cel file 405C. As described above, each of .cel files 405A, 405B, and 405C include intermediate results comprising a representative intensity value for each probe, generated from associated implementations of probe array 140 (i.e. may be denoted as array 140A, 140B, and 140C not illustrated in Figures). In the present example, manager 410 may obtain the selected files from one or more applications such as instrument control and image processing applications 372, one or more library files such as library files 274, memory storage devices 281 or 381, or other type of source or storage commonly used in the related art. Additionally, the selected .cel files may be communicated to input manager 410 over a network such as network 125, system bus 290 or 390, or other means known in the related art, thus allowing for local or remote communication of data to analysis application 380.

In the example of step 505, input manager 410 may initialize the process by creating or identifying data objects to be employed in the processing operations. Those of ordinary skill in the related art will appreciate that various object oriented programming languages such as C, C++, Java, and others are well suited for the creating and using data objects. Also, the selections from user 101 may identify a selection of one or more subsets of data from one or more .cel files 405 for data processing. User 101 may make the selections via one or more interfaces 246 implemented by analysis application 380 or instrument control and image analysis applications 372. Alternatively, the subsets of data may be pre-defined and represented in one or more files that could for instance be accessed from library files 274 or other experiment files. For example, the information could be passed to analysis application 380 as a string of characters using a command line interface or alternatively, interface 246 could include a GUI that allows user 101 to "drag and drop" graphical icons representing process steps and/or sets of data where the user may initiate processing according to the arrangement of icons via a button, other graphical element, or other means known in the art.

As illustrated in step 510, manager 410 opens an implementation of .cel 405 to be analyzed. Next, step 515 illustrates the step where manager 410 identifies the appropriate data to read and stores said data into the appropriate data object. Manger 410 may also receive data from one or more other files to retrieve parameters needed for processing. In some cases such information may be useful for identifying the appropriate intensity data to read from a .cel file. For example, probe and probe set location information may be represented in what may be referred to as a Probe Group File (.pgf) that may be received by manager 410 from library files 274 or other source as described above. Selected information from the .pgf file may be read stored in the same data object as the intensity data or in a different data object.

Manager 410 also determines one or more parameters necessary for the selected functional processing operations from the open .cel file. For example, the number and type of some or all of the parameters determined by manager 410 may depend upon the method later employed. For instance if analysis application implements a Quantile normalization method, manager 410 may evaluate each intensity value associated with each embodiment of .cel file 405 to generate a function representative of the distribution of intensities. The function may include a ranking each intensity value where there is 1 parameter associated with every probe represented in file .cel 405. Alternatively, if analysis application 380 implements a Sketch normalization method, it is not necessary to employ the computationally expensive process of evaluating all intensity values. Rather, manager 410 evaluates a sub-set or "sketch" of intensity values as representative of all values and used to generate the function. Input manager 410 then stores the determined parameters from the open implementation of .cel file 405 into a data object. Those of ordinary skill will appreciate that the data object used for storing the parameter information may be the same used for the intensity information or an independent data object. Some embodiments of manager 410 may temporarily store the data objects in cache memory 413.

Cache memory 413 is shown in FIG. 4 as internal to data analysis application 272, but those of ordinary skill in the related art will appreciate that this need not be so. As described, input manager 410 may extract the intensity values for selected subsets of probe sets specified by user 101 and place the values into a data object organized to store the selected probe set intensity values. Input manager 410 stores the data object into cache memory 413, and closes .cel file 405A as shown in step 520. For example, the data object organized to store the selected probe set intensity values maintains the original positional referencing with respect to probe array 140, where subsequent processes may be implemented that are "unaware" that only subsets of data are subject to analysis (i.e. the whole file is not represented). If there are additional .cel files 405 to process, such as .cel file 405B and .cel file 405C, as illustrated by decision element 523 then input manager 410 repeats the process described in steps 510-520 for each. Therefore, only one .cel file 405 is open at any point in time, reducing the memory required for parameter estimation, and further only the intensity values for the probe sets selected by user 101 are stored in memory reducing the requirements.

As illustrated in step 530, data normalizer 415 of analysis application 380 normalizes the selected subsets of probe sets associated with each .cel file 405 by employing one or more of the normalization methods described above that may also be user selected. For example, only the probe sets selected by user 101 and stored in the data objects are normalized. This is more efficient especially when user 101 is not interested in analyzing all of the data associated with an implementation of .cel file 405. Also, it is typically more efficient to apply normalization methods such as sketch normalization in comparison to quantile normalization because such methods are less computationally intensive. In addition, one embodiment of normalizer 415 performs the normalization dynamically, processing each selected set during the processing operation as opposed to pre-computing. Dynamic normalization allows normalizer 415 to employ more than one normalization method if desired and determined by user 101.

As illustrated in step 540, the normalized probe set intensity values may be processed by signal estimate generator 420 to determine the signal estimation for each probe and/or probe set in the data object. Signal estimate generator 420 may apply one or more methods or algorithms to the normalized probe set intensity values, such as for instance the PLIER algorithm described above that provides a probe-level estimation of signal intensity using an affinity value that represents a probe affinity to bind to its target molecule. For example, generator 420 produces a signal estimate for every selected intensity value represented in the data objects, illustrated as signal estimate data 423.

In some embodiments, affinity data 422 may be employed for certain selected methods described above to provide affinity values representative of each probes "affinity" to a target molecule under conditions that approximate the conditions that user 101 would process and image probe arrays 140. As previously described, "affinity" may refers to a probes hybridization performance to its target molecule. Affinity data 422 provides user 101 with the ability to analyze the data from a single .cel file using methods that otherwise may require multiple sets of .cel files to process that dynamically computes affinity values. Also, affinity data 422 may provide a consistent baseline for user 101 who is analyzing data from multiple .cel files and also save on the additional computation time required to dynamically generate the affinity data.

Signal estimate generator 420 may, in some embodiments, forward splice determiner 430. Step 550 illustrates the step of splice determiner 430 employing one or more methods to determine the presence and/or identify biological events such as alternative splicing events that include two or more alternative splice variants as described above. For example, annotator may process signal estimate data 423 using one or more methods selected by user 101. In the present example, user 101 may select the described ANOSVA method and produce splice variants data 427 that identifies the presence and/or concentration of alternative splice variants in the sample(s) used to generate .cel files 405.

Embodiments of analysis application 380 may direct signal estimate data 423, and/or splice variants data 427 to output manager 470. Output manager 470 may store data 423, data 427 or both in system memory 370, or other data storage element using one or more files or data structures. Analysis application 380 may also return the results to user 101 via one or more interfaces 246 or by other means known in the art. In some embodiments, the data may be transmitted over network 125 for presentation to user 101 in one or more interfaces 246 associated with a web browser as described above.

Output manager 470 may also export data 423, data 427 or both in one or more formats compatible with one or more different software platforms. Such a file may include a tab delimited text file or other simplified format as opposed to a format with increased complexity and reduced flexibility. Alternatively, such a file may include a more complex or proprietary format.

Embodiments of such software platforms may include third party analysis packages or data visualization software. For example, one possible data visualization platform may include what may be referred to as the Integrated Genome Browser (IGB) enabled to visually represent the results produced by analysis application 380. Additional examples of data visualization applications and methods may be found in U.S. patent application Ser. No. 10/423,404, titled "System, Method and Computer Program Product for Dynamic Display, and Analysis of Biological Sequence Data", filed Apr. 23, 2003, which is hereby incorporated by reference herein in its entirety for all purposes.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so on may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. Alternatively, functional elements, files, data structures, and so on may be described in the illustrated embodiments as located on separate computer or server systems that could in other embodiments be located on the same or single computer or server system. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

What is claimed is:

1. A method for analyzing data generated by probe arrays to identify alternative splicing events, comprising:
   (a) providing a computer with a computer program, wherein said program is designed to receive a first selection of at least two data files and a second selection identifying one or more subsets of intensity values within each data file, and wherein each subset comprises one or more of the intensity values acquired from a biological probe array;
   (b) opening one of the data files using the computer program;
   (c) identifying the intensity values associated with one or more of the selected subsets;
   (d) determining one or more parameters for processing by the computer program;
   (e) normalizing, with the computer program, the identified intensity values of the one or more selected subsets using the one or more parameters, wherein the normalization is based upon a normalization subset of intensity values, wherein the normalization subset comprises one or more intensity values of the one or more selected subsets, wherein intensity values of the normalization subset are selected without analyzing every value of the one or more selected subsets;
   (f) determining, using the computer program, a signal estimate for each identified intensity value;
   (g) storing the parameters and the signal estimates for the identified intensity values;
   (h) closing the data file;
   (i) repeating steps (b)-(h) with the computer program for each of the selected data files; and
   (j) processing each of the stored signal estimates for the identified intensity values using the one or more parameters and the computer program thereby identifying one or more alternative splicing events.

2. The method for analyzing of claim 1, wherein:
each selected subset comprises a number of intensity values that is less than a total number of intensity values represented in each data file.

3. The method for analyzing of claim 1, wherein:
the probe array comprises an exon array.

4. The method for analyzing of claim 3, wherein:
the exon array comprises a plurality of probe sets, wherein each of the probe sets interrogates an exon region of sequence.

5. The method for analyzing of claim 4, wherein:
the exon region is known or predicted.

6. The method for analyzing of claim 1, wherein step (g) further comprises:
using the computer program to store the parameters and the signal estimates for the identified intensity values in one or more data objects.

7. The method for analyzing of claim 6, wherein:
the data objects are stored in a cache memory.

8. The method for analyzing of claim 1, wherein:
the parameters comprise one or more measures of error.

9. The method for analyzing of claim 1, wherein:
the signal estimate is determined using a measure of affinity of a probe to a target molecule.

10. The method for analyzing of claim 1, further comprising:
   (k) providing the identified alternative splicing events to a user.

11. The method for analyzing of claim 10, wherein:
the identified alternative splicing events are provided in a user interface.

12. The method for analyzing of claim 11, wherein:
the user interface includes a graphical user interface.

13. A method for analyzing data generated by probe arrays to identify alternative splicing events, comprising:
   (a) providing a computer with a computer program, wherein said program receives a first selection of at least two data files and a second selection identifying one or more subsets of intensity values within each data file, wherein each subset comprises one or more of the intensity values acquired from a biological probe array;
   (b) opening one of the data files using the computer program;
   (c) identifying the intensity values associated with one or more of the selected subsets;
   (d) normalizing, with the computer program, the identified intensity values of the one or more selected subsets, wherein the normalization is based upon a normalization subset of intensity values, wherein the normalization subset comprises one or more intensity values of the one or more selected subsets, wherein intensity values of the normalization subset are selected without analyzing every value of the one or more selected subsets;
   (e) determining, using the computer program, a signal estimate for each identified intensity value;
   (f) storing the signal estimates for the identified intensity values in one or more data objects using the computer program;
   (g) closing the data file;
   (h) repeating steps (b)-(g) by using the computer program for each of the selected data files; and
   (i) using the computer program to process each of the stored signal estimates for the identified intensity values from the data objects, thereby identifying one or more alternative splicing events.

14. The method for analyzing of claim 13, wherein:
each data object stores the signal estimates of the intensity values associated with one of the selected subsets.

15. A system for analyzing data generated from probe arrays, comprising:
a computer that includes an application stored for execution in system memory that performs a method comprising:
   (a) receiving a first selection of at least two data files and a second selection identifying one or more subsets of intensity values within each data file, wherein each subset comprises one or more of the intensity values acquired from a biological probe array;
   (b) opening one of the data files;
   (c) identifying the intensity values associated with one or more of the selected subsets;
   (d) normalizing the identified intensity values of the one or more selected subsets, wherein the normalization is based upon a normalization subset of intensity values, wherein the normalization subset comprises one or more intensity values of the one or more selected subsets, wherein intensity values of the normalization subset are selected without analyzing every value of the one or more selected subsets;
   (e) determining a signal estimate for each identified intensity value,
   (f) storing the signal estimates for the identified intensity values from the open data file;

(g) closing the data file;
(h) repeating steps (b)-(g) for each of the selected data files; and
(i) processing each of the stored signal estimates for the identified intensity values to identify one or more alternative splicing events.

16. The system for analyzing of claim 15, wherein:
the signal estimates for the identified intensity values are stored in a data object.

17. A system for analyzing data generated by probe arrays, comprising:
a scanner that acquires a plurality of pixel intensity values from each of a plurality of probe arrays; and
a computer comprising:
a first application stored for execution in system memory that generates a data file associated with each of the probe arrays comprising a probe intensity value for each of a plurality of probes using the pixel intensity values; and
a second application stored for execution in system memory that performs a method comprising:
(a) receiving a first selection of at least two of the data files and a second selection identifying one or more subsets of probe intensity values within each data file, wherein each subset comprises one or more of the intensity values generated from data acquired from a probe array;
(b) opening one of the data files;
(c) identifying the intensity values associated with one or more of the selected subsets;
(d) determining one or more parameters for processing;
(e) normalizing the identified intensity values of the one or more selected subsets using the one or more parameters, wherein the normalization is based upon a normalization subset of intensity values, wherein the normalization subset comprises one or more intensity values of the one or more selected subsets, wherein intensity values of the normalization subset are selected without analyzing every value of the one or more selected subsets; characteristics of all intensity values from the one or more selected subsets;
(f) determining a signal estimate for each normalized intensity value,
(g) storing the parameters and the signal estimates for the identified intensity values;
(h) closing the data file;
(i) repeating steps (b)-(h) for each of the selected data files; and
(j) processing each of the stored signal estimates for the identified intensity values using the parameters to identify one or more alternative splicing events.

18. The system for analyzing of claim 17, wherein:
the computer includes a user workstation or a server.

19. The method for analyzing of claim 1, wherein:
the step of processing each of the stored signal estimates of the identified intensity values using the one or more parameters to identify one or more alternative splicing events is performed for each selected subset before the data file from which that subset was selected is closed.

20. The method for analyzing of claim 1, wherein:
the normalization subset comprises at least one intensity value from each probe set represented in the one or more selected subsets.

21. The method for analyzing of claim 1, wherein:
a compute farm performs steps (a)-(g) in parallel for a selection of at least two data files, wherein an application assigns each computer of the compute farm a subset of data, each computer processes that data in parallel with the other computers of the compute farm, and each computer returns processed results to the application.

22. The method for analyzing of claim 1, wherein:
the first selection of the at least two data files is made by a user.

23. The method for analyzing of claim 1, wherein:
the second selection of the one or more subsets of intensity values within each data file is made by a user.

24. The method for analyzing of claim 1, wherein:
the second selection of the one or more subsets is predefined in one or more files accessed by the program.

25. The method for analyzing of claim 1, wherein:
the one or more alternative splicing events are identified by, at least in part, use of two-way analysis of variance.

* * * * *